(12) United States Patent
Drewes et al.

(10) Patent No.: US 6,245,715 B1
(45) Date of Patent: Jun. 12, 2001

(54) SUBSTITUTED IMINOALKOXY-PHENYLURACILS, THE PRODUCTION AND USE THEREOF AS HERBICIDES

(75) Inventors: Mark Wilhelm Drewes; Roland Andree, both of Langenfeld (DE); Markus Dollinger, Overland Park, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/423,914
(22) PCT Filed: May 14, 1998
(86) PCT No.: PCT/EP98/02861
§ 371 Date: Nov. 16, 1999
§ 102(e) Date: Nov. 16, 1999
(87) PCT Pub. No.: WO98/54155
PCT Pub. Date: Dec. 3, 1998

(30) Foreign Application Priority Data

May 27, 1997 (DE) .............................. 197 22 031

(51) Int. Cl.⁷ .................... C07D 239/54; A01N 43/54
(52) U.S. Cl. ..................... 504/243; 544/311; 544/312
(58) Field of Search .................. 544/311, 312; 504/243

(56) References Cited

FOREIGN PATENT DOCUMENTS

| 195 24 617 | 1/1997 | (DE) . |
|---|---|---|
| 0 255 047 | 2/1998 | (EP) . |
| 93/11669 | 6/1993 | (WO) . |
| 95/06641 | 3/1995 | (WO) . |
| 95/25725 | 9/1995 | (WO) . |
| 96/24590 | 8/1996 | (WO) . |
| 97/01541 | 1/1997 | (WO) . |
| 97/05117 | 2/1997 | (WO) . |

*Primary Examiner*—John M. Ford
(74) *Attorney, Agent, or Firm*—Joseph C. Gil

(57) ABSTRACT

The invention relates to novel substituted iminoalkoxy-phenyluracils of the general formula (I)

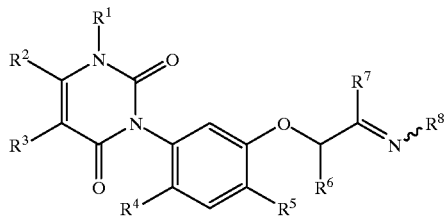

in which $R^1$ is hydrogen, amino or optionally substituted alkyl, $R^2$ is carboxyl, cyano, carbamoyl, thiocarbamoyl or alkyl or alkoxycarbonyl, the latter two being optionally substituted, $R^3$ is hydrogen, halogen or optionally substituted alkyl, $R^4$ is hydrogen, cyano, thiocarbamoyl or halogen, $R^5$ is cyano, thiocarbamoyl or halogen, $R^6$ is hydrogen or optionally substituted alkyl, $R^7$ is optionally substituted alkyl, and $R^8$ is hydroxyl, amino or a radical of the series alkyl, alkoxy, alkylamino, dialkylamino, alkylcarbonylamino, alkoxycarbonylamino, alkylsulfonylamino, alkenyl, alkynyl, alkenyloxy, alkynyloxy, aryl, aryloxy, arylamino, arylcarbonylamino, arylsufonylamino, arylalkyl, arylalkylamino, arylalkylcarbonylamino or arylalkylsulfonylamino, each of which is optionally substituted. The invention further relates to methods for producing said compounds and their use as herbicides.

4 Claims, No Drawings

SUBSTITUTED IMINOALKOXY-PHENYLURACILS, THE PRODUCTION AND USE THEREOF AS HERBICIDES

TECHNICAL FIELD OF THE INVENTION

The invention relates to novel substituted iminoalkoxy-phenyluracils, to processes for their preparation and to their use as herbicides.

BACKGROUND OF THE INVENTION

Certain substituted aryluracils, such as, for example, the compound 3-[4-chloro-2-fluoro-5-(2-oxo-propoxy)-phenyl]-1-methyl-6-trifluoromethyl-(1H,3H)-pyrimidine-2,4-dione, are already known from the (patent) literature (cf. EP 255047). However, these compounds have hitherto not obtained any particular importance.

DETAILED DESCRIPTION OF THE INVENTION

This invention, accordingly, provides novel substituted iminoalkoxy-phenyluracils of the general formula (I)

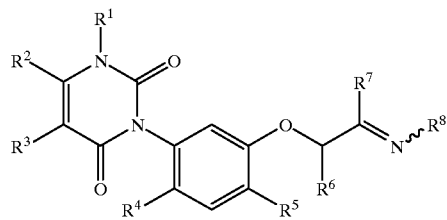

(I)

in which $R^1$ represents hydrogen, amino or optionally substituted alkyl, $R^2$ represents carboxyl, cyano, carbamoyl, thiocarbamoyl or represents in each case optionally substituted alkyl or alkoxycarbonyl, $R^3$ represents hydrogen, halogen or optionally substituted alkyl, $R^4$ represents hydrogen, cyano, thiocarbamoyl or halogen, $R^5$ represents cyano, thiocarbamoyl or halogen, $R^6$ represents hydrogen or optionally substituted alkyl, $R^7$ represents optionally substituted alkyl, and $R^8$ represents hydroxyl, amino or represents in each case an optionally substituted radical from the group consisting of alkyl, alkoxy, alkylamino, dialkylamino, alkylcarbonylamino, alkoxycarbonylamino, alkylsulphonylamino, alkenyl, alkinyl, alkenyloxy, alkinyloxy, aryl, aryloxy, arylamino, arylcarbonylamino, arylsulphonylamino, arylalkyl, arylalkylamino, arylalkylcarbonylarnino or arylalkylsulphonylamino.

The novel substituted iminoalkoxy-phenyluracils of the general formula (I) are obtained when substitued oxoalkoxy-phenyluracils of the general formula (II)

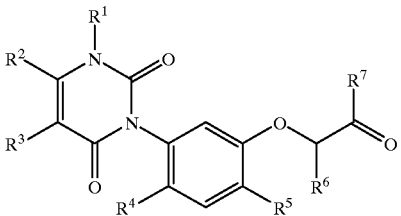

(II)

in which $R^1$, $R^2$, $R^3$, $R^4$, $R^5$, $R^6$ and $R^7$ are as defined above, are reacted with amino compounds of the general formula (III)

$$H_2N-R^8 \quad \text{(III)}$$

in which $R^8$ is as defined above or with acid adducts of compounds of the general formula (III)

if appropriate in the presence of a reaction auxiliary and if appropriate in the presence of a diluent, and electrophilic or nucleophilic substitution reactions or addition reactions within the scope of the definition of the substituents are subsequently carried out, if appropriate.

The compounds of the general formula (I) can be converted by customary methods into other compounds of the general formula (I) in accordance with the above definition, for example by amination or alkylation (for example $R^1$: H→NH$_2$, H→CH$_3$), reaction with dicyanogen or hydrogen sulphide (for example $R^5$: Br→CN, CN→CSNH$_2$, cf. the Preparation Examples).

The novel substituted iminoalkoxy-phenyluracils of the general formula (I) have strong and selective herbicidal activity.

In the definitions, the saturated or unsaturated hydrocarbon chains, such as alkyl, alkenyl or alkinyl, are in each case straight-chain or branched.

Halogen generally represents fluorine, chlorine, bromine or iodine, preferably fluorine, chlorien or bromine, in particular fluorine or chlorine.

The invention preferably provides compounds of the formula (I) in which $R^1$ represents hydrogen, amino or optionally cyano-, fluorine-, chlorine- or $C_1$–$C_4$-alkoxy-substituted $C_1$–$C_6$-alkyl, $R^2$ represents carboxyl, cyano, carbamoyl, thiocarbamoyl or represents in each case optionally cyano-, fluorine-, chlorine- or $C_1$–$C_4$-alkoxy-substituted $C_1$–$C_4$-alkyl or $C_1$–$C_4$-alkoxycarbonyl, $R^3$ represents hydrogen, fluorine, chlorine, bromine or optionally fluorine- or chlorine-substituted $C_1$–$C_4$-alkyl, $R^4$ represents hydrogen, cyano, thiocarbamoyl, fluorine, chlorine or bromine, $R^5$ represents cyano, thiocarbamoyl, fluorine, chlorine or bromine, $R^6$ represents hydrogen or optionally cyano-, fluorine-, chlorine- or $C_1$–$C_4$-alkoxy-substituted $C_1$–$C_6$-alkyl, $R^7$ represents optionally cyano-, fluorine-, chlorine- or $C_1$–$C_4$-alkoxy-substituted $C_1$–$C_6$-alkyl, and $R^8$ represents hydroxyl, represents amino or represents in each case optionally carboxyl-, cyano-, halogen-, $C_1$–$C_4$-alkoxy- or $C_1$–$C_4$-alkoxy-carbonyl-substituted alkyl, alkoxy, alkylamino, dialkylamino, alkylcarbonylamino, alkoxycarbonylamino or alkylsulphonylamino having in each case 1 to 6 carbon atoms, $R^8$ furthermore represents in each case optionally halogen-substituted alkenyl, alkinyl, alkenyloxy or alkinyloxy having in each case 3 to 6 carbon atoms, or $R^8$ furthermore represents in each case optionally nitro-, cyano-, carboxyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted aryl, aryloxy, arylamino, arylcarbonylamino, arylsulphonylamino, arylalkyl, arylalkylamino, arylalkylcarbonylamino or arylalkylsulphonylamino having in each case 6 or 10 carbon atoms in the aryl moiety and optionally 1 to 4 carbon atoms in the alkyl moiety.

The invention in particular relates to compounds of the formula (I) in which $R^1$ represents hydrogen, represents amino or represents in each case optionally cyano-, fluorine-, chlorine-, methoxy- or ethoxy-substituted methyl, ethyl, n- or i-propyl, n-, i-, s- or t-butyl, $R^2$ represents carboxyl, cyano, carbamoyl, thiocarbamoyl or represents in each case optionally cyano-, fluorine-, chlorine-, methoxy- or ethoxy-substituted methyl, ethyl, methoxycarbonyl or ethoxycarbonyl, $R^3$ represents hydrogen, fluorine, chlorine, bromine or represents in each case optionally fluorine- or chlorine-substituted methyl or ethyl, $R^4$ represents hydrogen, fluorine or chlorine, $R^5$ represents cyano, thiocarbamoyl, chlorine or bromine, $R^6$ represents hydrogen or represents in each case optionally cyano-, fluorine-, chlorine-, methoxy- or ethoxy-substituted methyl, ethyl, n- or i-propyl, n-, i-, s- or t-butyl, $R^7$ represents in each case optionally cyano-, fluorine-, chlorine-, methoxy- or ethoxy-substituted methyl, ethyl, n- or i-propyl, n-, i-, s- or t-butyl, and $R^8$ represents hydroxyl, represents amino, or represents in each case optionally carboxyl-, cyano-, fluorine-, chlorine-, methoxy-, ethoxy-, n- or i-propoxy-, methoxycarbonyl-, ethoxycarbonyl-, n- or i-propoxycarbonyl-substituted methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i-, s- or t-butylamino, dimethylamino, diethylamino, acetylamino, propionylamino, methoxycarbonylamino, ethoxycarbonylamino, methylsulphonylamino or ethylsulphonylamino, or $R^8$ furthermore represents in each case optionally fluorine-, chlorine- or bromine-substituted propenyl, butenyl, propinyl, butinyl, propenyloxy, butenyloxy, propinyloxy or butinyloxy, or $R^8$ furthermore represents in each case optionally nitro-, cyano-, carboxyl-, fluorine-, chlorine-, bromine-methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy-, trifluoromethoxy-substituted phenyl, phenoxy, phenylamino, benzoylamino, phenylsulphonylamino, benzyl, benzylamino, benzylcarbonylamino or benzylsulphonylamino.

The abovementioned general or preferred radical definitions apply both to the end products of the formula (I) and, correspondingly, to the starting materials or intermediates required in each case for the preparation. These radical definitions can be combined with each other as desired, i.e. including combinations between the given preferred ranges.

Using, for example, 3-[4-chloro-2-fluoro-5-(2-oxopropoxy)-phenyl]-1-methyl-6-trifluoromethyl-(1H,3H)-pyrimidine-2,4-dione and O-methylhydroxylamine as starting materials, the course of the reaction in the preparation process according to the invention can be illustrated by the following scheme:

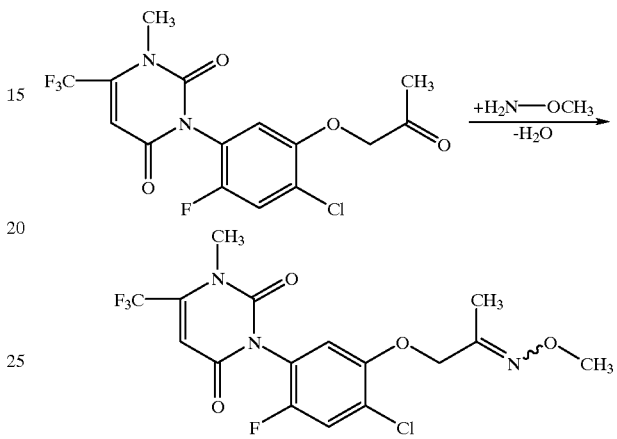

The formula (II) provides a general definition of the oxoalkoxy-phenyluracils to be used as starting materials in the process according to the invention for preparing compounds of the formula (I). In the formula (II), $R^1$, $R^2$, $R^3$, $R^4$, $R^5$, $R^6$ and $R^7$ preferably or in particular have those meanings which have already been mentioned above, in connection with the description of the compounds of the formula (I) according to the invention as being preferred or as being particularly preferred for $R^1$, $R^2$, $R^3$, $R^4$, $R^5$, $R^6$ and $R^7$.

The starting materials of the general formula (II) are known and/or can be prepared by known processes (cf. EP 255047, Preparation Examples).

The formula (III) provides a general definition of the amino compounds further to be used as starting materials in the process according to the invention. In the formula (III), $R^8$ preferably or in particular has that meaning which has already been mentioned above, in connection with the description of the compounds of the formula (I) according to the invention, as being preferred or as being particularly preferred for $R^8$. It is also preferably possible to use adducts of compounds of the formula (III) with strong acids, in particular with mineral acids, such as, for example, hydrogen chloride, hydrogen bromide or sulphuric acid, in the process according to the invention.

The starting materials of the general formula (III) are known chemicals for synthesis.

Suitable reaction auxiliaries for the process according to the invention for preparing compounds of the formula (I) are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide, or potassium methoxide, ethoxide, n- or 1-propoxide, n-, i-, s- or t-butoxide; furthermore also basic organic nitrogen compounds, such as, for example, trimethylamine, triethylamine, tripropylamine tributylamine, ethyl-diisopropylamine, N,N-dimethylcyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-Dimethyl-, 2,6-dimethyl-, 3,4-dimethyl- and 3,5-dimethyl-pyridine, 5-ethyl-2-methylpyridine, 4-dimethylamino-pyridine, N-methylpiperidine, 1,4-diazabicyclo[2,2,2]octane (DABCO), 1,5-diazabicyclo[4,3,0]-non-5-ene (DBN), or 1,8 diazabicyclo[5,4,0]-undec-7-ene (DBU).

Suitable diluents for carrying out the process according to the invention are, in particular, inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diusopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters such as methyl acetate or ethyl acetate, sulphoxides, such as diemethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

When carrying out the process according to the invention, the reaction temperatures can be varied within a relatively wide range. In general, the reaction is carried out at temperaturesh between 0° C. and 150° C., preferably between 10° C. and 120° C.

The process according to the invention is generally carried out under atmospheric pressure. However, it is also possible to carry out the process according to the invention under elevated or reduced pressure—in general between 0.1 bar and 10 bar.

In carrying out the process according to the invention, the starting materials are generally employed in approximately equimolar amounts. However, it is also possible to employ a relatively large excess of one of the components. The reaction is generally carried out in a suitable diluent in the presence of a reaction auxiliary and the reaction mixture is generally stirred for a number of hours at the temperature required. Work-up is carried out by customary methods (cf. the Preparation Examples).

The active compounds according to the invention can be used as defoliants, desiccants, haulm killers and, especially, as weed-killers. By weeds in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis. Papaver, Centaurea, Trifolium, Ranunculus and Taraxacum.

Dicotyledonous cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and squares with or without tree plantings. Equally, the compounds can be employed for the control of weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective control of weeds in annual cultures.

The compounds of the formula (I) according to the invention are suitable in particular for the selective control of monocotyledonous and dicotyledonous weeds in monocotyledonous and dicotyledonous crops, both pre-emergence and post-emergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

If the extender used is water, it is also possible to employ, for example, organic solvents as auxiliary solvents. Suitable liquid solvents are essentially the following: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For the control of weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, asulam, atrazine, azimsulfuron, benazolin, benfuresate, bensulfuron(-methyl), bentazon, benzofenap, benzoylprop(-ethyl), bialaphos, bifenox, bromobutide, bromofenoxim, bromoxynil, butachlor, butylate, cafenstrole, carbetamide, chlomethoxyfen, chloramben, chloridazon, chlorimuron(-ethyl), chlornitrofen, chlorsulfuron, chlortoluron, cinmethylin, cinosulfuron, clethodim, clodinafop(-propargyl), clomazone, clopyralid, clopyrasulfuron, cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethametsulfuron(-methyl), ethofumesate, ethoxyfen, etobenzanid, fenoxaprop(-ethyl), flamprop(-isopropyl), flamprop(-isopropyl-L), flamprop(-methyl), flazasulfuron, fluazifop(-butyl), flumetsulam, flumiclorac(-pentyl), flumioxazin, flumipropyn, fluometuron, fluorochloridone, fluoroglycofen(-ethyl), flupoxam, flupropacil, flurenol, fluridone, fluroxypyr, flurprimidol, flurtamone, fomesafen, glufosinate(-ammonium), glyphosate(-isopropylammonium), halosafen, haloxyfop (-ethoxyethyl), hexazinone, imazamethabenz(-methyl), imazamethapyr, imazamox, imazapyr, imazaquin, imazethapyr, imazosulfuron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, metoxuron, metribuzin, metsulfuron(-methyl), molinate, monolinuron, naproanilide, napropamide, neburon, nicosulfuron, norflurazon orbencarb, oryzalin, oxadiazon, oxyfluorfen, paraquat, pendimethalin, phenmedipham, piperophos, pretilachlor, primisulfuron(-methyl), prometryn, propachlor, propanil, propaquizafop, propyzamide, prosulfocarb, prosulfuron, pyrazolate, pyrazosulfuron(-ethyl), pyrazoxyfen, pyributicarb, pyridate, pyrithiobac(-sodium), quinchlorac, quinmerac, quizalofop(-ethyl), quizalofop(-p-tefuryl), rimsulfuron, sethoxydim, simazine, simetryn, sulcotrione, sulfentrazone, sulfometuron(-methyl), sulfosate, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

A mixtures with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the following examples.

PREPARATION EXAMPLES

Example 1

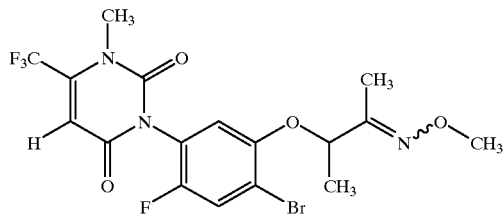

A mixture of 1.5 g (3.31 mmol) of 3-[4-bromo-2-fluoro-5-(1-methyl-2-oxo-propoxy)-phenyl]-1-methyl-6-trifluoromethyl-(1H,3H)-pyrimidine-2,4-dione, 0.30 g (3.31 mmol) of O-methyl-hydroxylamine, 0.30 g of sodium acetate and 20 ml of ethanol is stirred at room temperature (approximately 20° C.) for one hour and then concentrated under water-pump vacuum. The residue is taken up in water, adjusted to a pH between 2 and 3 using 1N hydrochloric acid and shaken with diethyl ether. The organic phase is washed with water, dried with sodium sulphate and filtered. The solvent is then carefully distilled off from the filtrate under water pump vaccum.

This gives 1.5 g (94% of theory) of 3-[4-bromo-2-fluoro-5-(1-methyl-2-methoximino-propoxy)-phenyl]-1-methyl-6-trifluoromethyl-(1H,3H)-pyrimidine-2,4-dione as an amorphous residue.

Example 2

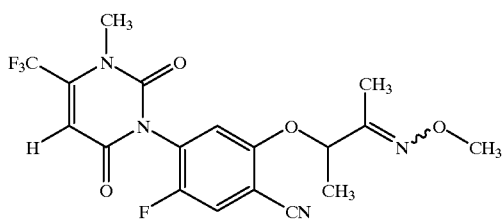

Under an atmosphere of argon, a mixture of 0.90 g (1.86 mmol) of 3-[4-bromo-2-fluoro-5-(1-methyl-2-methoximino-propoxy)-phenyl]-1-methyl-6-trifluoromethyl-(1H,3H)-pyrimidine-2,4-dione, 0.11 g of zinc(II) cyanide, 0.08 g of tetrakis-(triphenylphosphine)-palladium(0) and 10 ml of N,N-dimethyl-formamide is heated at 80° C.–90° C. for 8 hours. After addition of a further 0.1 g of zinc(II) cyanide and 0.07 g of tetrakis-(triphenylphosphine)-palladium(0), the mixture is heated at 80° C.–90° C. for a further 30 hours. The mixture is then shaken with 1N hydrochloric acid and ethyl acetate, and the organic phase is separated off and concentrated under water pump vaccum. The residue is purified by column chromatography (silica gel, hexane/ethyl acetate, vol. 4/1).

This gives 0.40 g (50% of theory) of 3-[4-cyano-2-fluoro-5-(1-methyl-2-methoximino-propoxy)-phenyl]-1-methyl-6-trifluoromethyl-(1H,3H)-pyrimidine-2,4-dione as an amorphous product.

Similarly to the Preparation Examples 1 and 2, and in accordance with the general description of the preparation process according to the invention, it is also possible to prepare, for example, the compounds of the formula (I) listed in Table 1 below.

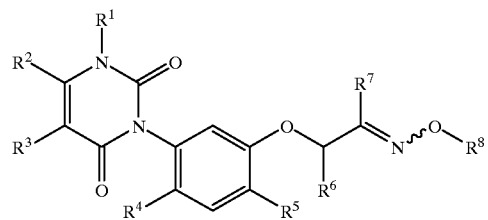

(I)

TABLE 1

Examples of compounds of the formula (I)

| Ex. No. | $R^1$ | $R^2$ | $R^3$ | $R^4$ | $R^5$ | $R^6$ | $R^7$ | $R^8$ | Physical Data |
|---|---|---|---|---|---|---|---|---|---|
| 3 | $CH_3$ | $CF_3$ | H | F | Br | $CH_3$ | $CH_3$ | $OC_2H_5$ | (amorph.) |
| 4 | $CH_3$ | $CF_3$ | H | F | CN | $CH_3$ | $CH_3$ | $OC_2H_5$ | m.p. 115° C. |
| 5 | $CH_3$ | $CF_3$ | H | F | Cl | $CH_3$ | $CH_3$ | $OC_3H_7$-i | |
| 6 | $CH_3$ | $CF_3$ | H | F | CN | $CH_3$ | $CH_3$ | $OC_3H_7$-i | |
| 7 | $CH_3$ | $CF_3$ | H | F | Cl | $CH_3$ | $CH_3$ | $NHC_6H_5$ | |
| 8 | $CH_3$ | $CF_3$ | H | F | Cl | $CH_3$ | $CH_3$ | $NHSO_2CH_3$ | |
| 9 | $CH_3$ | $CF_3$ | H | F | Cl | $CH_3$ | $CH_3$ | OH | |
| 10 | $CH_3$ | $CF_3$ | H | F | Cl | $CH_3$ | $CH_3$ | $NHCOCH_3$ | |
| 11 | $CH_3$ | $CF_3$ | H | F | Cl | $CH_3$ | $CH_3$ | $NH_2$ | |
| 12 | $CH_3$ | $CF_3$ | Cl | F | CN | $CH_3$ | $CH_3$ | $OC_2H_5$ | |
| 13 | $CH_3$ | $CF_3$ | $CH_3$ | F | CN | $CH_3$ | $CH_3$ | $OC_3H_7$-i | |
| 14 | $CH_3$ | $CF_3$ | H | F | CN | H | $CH_3$ | $N(CH_3)_2$ | |
| 15 | $CH_3$ | $CF_3$ | H | F | CN | H | $CH_3$ | —O—CH₂—CH=CH₂ | |
| 16 | $CH_3$ | $CF_3$ | H | F | —C(=S)NH₂ | $CH_3$ | $CH_3$ | $OCH_3$ | |
| 17 | $CH_3$ | $CF_3$ | H | F | Br | $CH_3$ | $CH_3$ | —NH—C₆H₄—Cl (4-Cl) | m.p.: 164° C. |
| 18 | $CH_3$ | $CF_3$ | H | F | Br | $CH_3$ | $CH_3$ | —NH—C₆H₄—Cl (2-Cl) | (amorph.) |

TABLE 1-continued

Examples of compounds of the formula (I)

| Ex. No. | R¹ | R² | R³ | R⁴ | R⁵ | R⁶ | R⁷ | R⁸ | Physical Data |
|---|---|---|---|---|---|---|---|---|---|
| 19 | $CH_3$ | $CF_3$ | H | F | Br | $CH_3$ | $CH_3$ | —NH—C₆H₅ | m.p.: 133° C. |
| 20 | $CH_3$ | $CF_3$ | H | F | Br | $CH_3$ | $CH_3$ | —NH—(3-Cl-C₆H₄) | m.p.: 170° C. |
| 21 | $CH_3$ | $CF_3$ | H | F | CN | $CH_3$ | $CH_3$ | —NH—(4-Cl-C₆H₄) | m.p.: 180° C. |
| 22 | $CH_3$ | $CF_3$ | H | F | CN | $CH_3$ | $CH_3$ | —NH—(2-Cl-C₆H₄) | m.p.: 150° C. |

STARTING MATERIALS OF FORMULA (II)

Example II-1

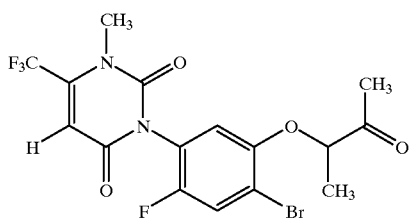

A mixture of 2.8 g (6.38 mmol) of 3-[4-bromo-2-fluoro-5-(1-methyl-2-oxo-propoxy)-phenyl]-6-trifluoromethyl-(1H,3H)-pyrimidine-2,4-dione, 0.10 g (8 mmol) of dimethyl sulphate, 1 g of potassium carbonate and 30 ml of acetone is heated under reflux for 45 minutes and subsequently concentrated under water pump vacuum. The residue is shaken with 1N hydrochloric acid and ethyl acetate and concentrated under water pump vacuum. The residue that remains is purified by column chromatography (silica gel, hexane/ethyl acetate, vol. 4/1).

This gives 2.0 g (69% of theory) of 3-[4-bromo-2-fluoro-5-(1-methyl-2-oxo-propoxy)-phenyl]-1-methyl-6-trifluoromethyl-(1H,3H)-pyrimidine-2,4-dione of melting point 119° C.

PRECURSORS FOR EXAMPLE (II-1)

Precursor 1

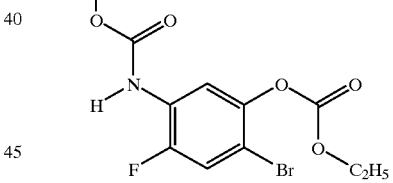

23.9 g (0.22 mol) of ethyl chloroformate are added dropwise with stirring to a mixture of 20 g (0.97 mol) of 4-bromo-2-fluoro-5-hydroxyaniline, 17.4 g (0.22 mol) of pyridine and 200 ml of methylene chloride which had been cooled to 0° C., and the reaction mixture is then stirred for another hour at from 0° C. to 5° C. The mixture is subsequently shaken with 1N hydrochloric acid, and the organic phase is separated off, dried with sodium sulphate and filtered. The filtrate is concentrated under water pump vacuum, the residue is digested with petroleum ether and the resulting crystalline product is isolated by filtration with suction.

This gives 30.4 g (90% of theory) of N-(4-bromo-2-fluoro-5-ethoxycarbonyloxyphenyl) O-ethyl carbamate of melting point 79° C.

Precursor 2

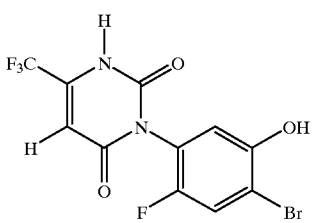

A mixture of 22 g (0.87 mol) of ethyl 3-amino-4,4,4-trifluoro-crotonate, 30.4 g (0.87 mol) of N-(4-bromo-2-fluoro-5-ethoxycarbonyloxy-phenyl) O-ethyl carbamate, 4.7 g of sodium hydride and 50 ml of N,N-dimethyl-formamide is heated at 125° C. for 2 hours. After cooling, the mixture is shaken with 1N hydrochloric acid/ethyl a cetate, and the organic phase is separated off, dried with sodium sulphate and filtered. The filtrate is concentrated under water pump vacuum and the residue is purified by column chromatography (silica el, chloroformethyl acetate, vol. 7/3).

This gives 12.6 g (37% of theory) of 3-(4-bromo-2-fluoro-5-hydroxy-phenyl)-6-trifluoromethyl-(1H,3H)-pyrimidine-2,4-dione as an amorphous product.

Precursor 3

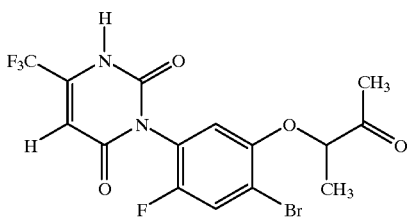

A mixture of 3.0 g (8.13 mmol) of 3-(4-bromo-2-fluoro-5-hydroxy-phenyl)-6-trifluoromethyl-(1H,3H)-pyrimidine-2,4-dione, 1.06 g (10 mmol) of 3-chloro-2-butanone, 2.34 g of potassium carbonate and 50 ml of acetonitrile is heated under reflux for 3 hours and subsequently concentrated under water pump vacuum. The residue is stirred with 1N hydrochloric acid/petroleum ether and the resulting crystalline product is isolated by filtration with suction.

This gives 3.1 g (87% of theory) of 3-[4-bromo-2-fluoro-5-(1-methyl-2-oxopropoxy)-phenyl]-6-trifluoromethyl-(1H,3H)-pyrimidine-2,4-dione of melting point 183° C.

USE EXAMPLES

Example A

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After approximately 24 hours, the soil is watered with the preparation of active compounds. The amount of water per unit area is advantageously kept constant. The concentration of active compound in the preparation is immaterial, only the active compound application rate per unit area matters.

After three weeks, the degree of damage to the plants is rated in % damage by comparison to the development of the untreated control.

The figures denote:

0%=no effect (like untreated control)

100%=total destruction

In this test, at application rates of from 60 to 125 g/ha, the compounds of Preparation Example 1, 2, 3 and 4, for example, exhibit very strong activity against weeds such as Echinochloa (100%), Setaria (100%), Abutilon (100%), Amaranthus (100%), Galium (100%), Solanum (100%), Alopecurus (100%) and Sorghum (100%), and some of them are tolerated well by crop plants, such as, for example, cotton (0%).

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound such that the particular desired amounts of active compound are applied per unit area. The concentration of the spray liquor is chosen so that the particular desired amounts of active compound are applied in 1000 l of water/ha.

After three weeks, the degree of damage to the plants is rated in % damage by comparison to the development of the untreated control.

The figures denote:

0%=no effect (like untreated control)

100%=total destruction

In this test, at application rates of from 15 g to 60 g/ha, the compounds of Preparation Example 1, 2, 3 and 4, for example, exhibit very strong activity against weeds such as Abutilon (100%), Datura (100%), Solanum (100%), Viola (100%), Echinochloa (80–100%), Setaria (80–100%), Sorhum (70–100%), Amaranthus (100%), Ipomoea (100%) and Veronica (100%), and some of them are tolerated well by crop plants, such as, for example, wheat (0%).

What is claimed is:

1. A substituted iminoalkoxy-phenyluracil of the general formula (I),

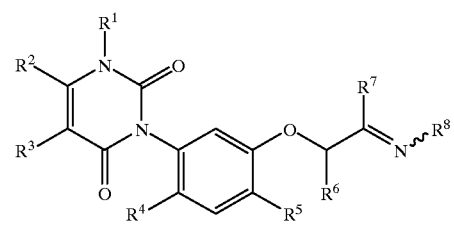

wherein $R^1$ represents hydrogen, amino, $C_1$–$C_8$ alkyl, or cyano-, fluorine-, chlorine- or $C_1$–$C_4$-alkoxy-substituted $C_1$–$C_6$-alkyl, $R^2$ represents carboxyl, cyano, carbamoyl, thiocarbamoyl, $C_1$–$C_4$-alkyl, $C_1$–$C_4$-alkoxycarbonyl, or represents in each case cyano-, fluorine-, chlorine- or $C_1$–$C_4$-alkoxy-substituted $C_1$–$C_4$-alkyl or $C_1$–$C_4$-alkoxycarbonyl, $R^3$ represents hydrogen, halogen, $C_1$–$C_4$-alkyl, or flourine- or chlorine-substituted $C_1$–$C_4$-alkyl, $R^4$ represents hydrogen, cyano, thiocarbamoyl or halogen, $R^5$ represents cyano, thiocarbamoyl or halogen, $R^6$ represents hydrogen, $C_1$–$C_6$-alkyl, or cyano-, fluorine-, chlorine- or $C_1$–$C_4$-alkoxyl-substituted $C_1$–$C_6$-alkyl, $R^7$ represents $C_1$–$C_6$ alkyl, or cyano-, fluorine, chlorine- or $C_1$–$C_1$-alkoxy-substituted $C_1$–$C_6$-alkyl, and $R^8$ represents hydroxyl; amino; a radical selected from the group consisting of $C_1$–$C_6$-alkyl, $C_1$–$C_6$-alkoxy, $C_1$–$C_6$-alkylamino, di($C_1$–$C_6$)-alkylamino, $C_1$–$C_6$-alkylcarbonylamino, $C_1$–$C_6$-alkoxycarbonylamino, $C_1$–$C_6$-alkylsulphonylamino, $C_3$–$C_6$-alkenyl, $C_3$–$C_6$-alkynyl, $C_3$–$C_6$-alkenyloxy, $C_3$–$C_6$-alkynyloxy, $C_6$–$C_{10}$-aryl, $C_6$–$C_{10}$-aryloxy, $C_6$–$C_{10}$-arylamino, $C_6$–$C_{10}$-arylcarbonylamino, $C_6$–$C_{10}$-arylsuphonylamino, $C_6$–$C_{10}$-aryl-$C_1$–$C_4$-alkyl, $C_6$–$C_{10}$-aryl-$C_1$–$C_4$-alkylamino, $C_6$–$C_{10}$-aryl-$C_1$–$C_4$-alkylcarbonylamino and $C_6$–$C_{10}$-aryl-$C_1$–$C_4$-alkylsulphonylamino; a radical selected from the group consisting of carboxyl-, cyano-, halogen-, $C_1$–$C_4$-alkoxy- or $C_1$–$C_4$-allkoxy-carbonyl-substituted $C_1$–$C_6$-alkyl, $C_1$–$C_6$-alkoxy, $C_1$–$C_6$-alkylamino, di($C_1$–$C_6$)-alkylamino, $C_1$–$C_6$-alkylcarbonylamino, $C_1$–$C_6$-alkoxycarbonylamino and $C_1$–$C_6$-alkylsulphonylamino; a radical selected from the group consisting of halogen-substituted $C_3$–$C_6$-alkenyl, $C_3$–$C_6$-alkynyl, $C_3$–$C_6$-alkenyloxy and $C_3$–$C_6$-alkynyloxy; or a radical selected from the aroup consisting of nitro-, cyano-, carboxyl-, halogen-, $C_1$–$C_4$-alkyl-, $C_1$–$C_4$-halogenoalkyl-, $C_1$–$C_4$-alkoxy- or $C_1$–$C_4$-halogenalkoxy-substituted $C_6$–$C_{10}$-aryl, $C_6$–$C_{10}$-aryloxy, $C_6$–$C_{10}$-arylamino, $C_6$–$C_{10}$-arylcarbonylamino, $C_6$–$C_{10}$-arylsulphonylamino, $C_6$–$C_{10}$-aryl-$C_1$–$C_4$-alkyl, $C_6$–$C_{10}$-aryl-$C_1$–$C_4$-alkylamino, $C_6$–$C_{10}$-aryl-$C_1$–$C_4$-alkylcarbonylamino and $C_6$–$C_{10}$-aryl-$C_1$–$C_4$-alkylsulphonylamino.

2. A process for preparing a substituted iminoalkoxyphenyluracil of the general formula (I)

(I)

wherein
$R^1$, $R^2$, $R^3$, $R^4$, $R^5$, $R^6$, $R^7$ and $R^8$ are as defined in claim 1, comprising the step of reacting a substituted oxoalkoxyphenyluracil of the general formula (II)

(II)

wherein
$R^1$, $R^2$, $R^3$, $R^4$, $R^5$, $R^6$ and $R^7$ are as defined above
with an amino compound of the general formula (III)

$$H_2N-R^8 \quad (III)$$

wherein
$R^8$ is as defined above
or with an acid adduct of the compound of the general formula (III).

3. A herbicidal composition, comprising at least one substituted iminoalkoxy-phenyluracil of the formula (I) according to claim 1 and one or more extenders and/or surfactants.

4. A method for controlling undesirable plants, comprising the step of allowing a herbicidally effective amount of a substituted iminoalkoxy-phenyluracil of the formula (I) according to claim 1 to act on at least one of undesirable plants and their habitat.

* * * * *